US012731695B2

(12) United States Patent
Gurpur et al.

(10) Patent No.: US 12,731,695 B2
(45) Date of Patent: Sep. 8, 2026

(54) AUTOMATED SUSCEPTIBILITY IDENTIFICATION AND ALERTING IN INFECTIOUS DISEASE OUTBREAKS

(71) Applicant: CERNER INNOVATION, INC., Kansas City, KS (US)

(72) Inventors: Praveen Bhat Gurpur, Bengaluru (IN); Karteek Alluvada, Bengaluru (IN)

(73) Assignee: CERNER INNOVATION, INC., Kansas City, MO (US)

( * ) Notice: Subject to any disclaimer, the term of this patent is extended or adjusted under 35 U.S.C. 154(b) by 346 days.

(21) Appl. No.: 17/097,700

(22) Filed: Nov. 13, 2020

(65) Prior Publication Data

US 2022/0157474 A1 May 19, 2022

(51) Int. Cl.
*G16H 50/80* (2018.01)
*G16H 10/60* (2018.01)
*G16H 50/30* (2018.01)

(52) U.S. Cl.
CPC ............ *G16H 50/80* (2018.01); *G16H 10/60* (2018.01); *G16H 50/30* (2018.01)

(58) Field of Classification Search
None
See application file for complete search history.

(56) References Cited

U.S. PATENT DOCUMENTS 7,457,731 B2 11/2008 Rao
11,056,242 B1 * 7/2021 Jain ........................ G16H 10/60
11,127,506 B1 * 9/2021 Jain ........................ H04W 4/021
11,456,080 B1 * 9/2022 Jain ...................... A61B 5/4815
11,504,011 B1 * 11/2022 Jain .......................... G06N 5/04
2006/0036619 A1 * 2/2006 Fuerst .................... G16H 50/80
2015/0100330 A1 * 4/2015 Shpits .................... G16H 50/80 705/2
2017/0316181 A1 11/2017 Kass-hout et al.
2018/0181713 A1 * 6/2018 Pillarisetty ............. G16H 10/60
2018/0279880 A1 * 10/2018 Bacchi ................... G16H 20/30
2018/0322255 A1 * 11/2018 Connell, II ............ G16H 50/20

(Continued)

OTHER PUBLICATIONS

Schnake-Mahl, Identifying Patients with Increased Risk of Severe Covid-19 Complications: Building an Actionable Rules-Based Model for Care Teams, NEJM, May 4, 2020. (Year: 2020).*

(Continued)

*Primary Examiner* — Anne-Marie K Alderson
(74) *Attorney, Agent, or Firm* — Invoke

(57) ABSTRACT

Methods, systems, and computer-readable media are disclosed herein for automated susceptibility identification and alerting. An occurrence of an outbreak of an infectious disease occurring at a particular time or time range and at a particular location is determined. In response to determining the occurrence of the outbreak, patient information comprising location information and medical history information is automatically scanned. Patients who are within a predetermined range of the particular location of the outbreak and who have at least one high risk factor corresponding to the outbreak are identified using the patient information. A notification to at least one of the patients who are within the predetermined range and who have the at least one high risk factor corresponding to the outbreak is provided. The notification comprises a representation of an increased risk to the outbreak.

20 Claims, 4 Drawing Sheets

(56) References Cited

U.S. PATENT DOCUMENTS

| | | | | |
|---|---|---|---|---|
| 2019/0088159 | A1* | 3/2019 | Minturn | G16H 50/30 |
| 2019/0252078 | A1* | 8/2019 | Schubert | G06N 3/09 |
| 2019/0279069 | A1* | 9/2019 | Bastide | G16H 20/10 |
| 2020/0105418 | A1* | 4/2020 | Mei | G16H 50/50 |
| 2020/0211692 | A1* | 7/2020 | Kalafut | G06N 20/00 |

OTHER PUBLICATIONS

Sattar et al., Obesity Is a Risk Factor for Severe COVID-19 Infection, Circulation, vol. 142 No 1, pp. 4-6; Published online Apr. 22, 2020 (Year: 2020).*

* cited by examiner

AUTOMATED SUSCEPTIBILITY IDENTIFICATION AND ALERTING IN INFECTIOUS DISEASE OUTBREAKS

BACKGROUND

In epidemiology, an outbreak of a sudden increase in occurrences of a disease in a particular time and place may affect a small and localized group, or it may affect thousands of people across a large land mass. Prevention and control measures are usually implemented when there is an occurrence of an outbreak. Examples of such measures include promoting good hygiene and hand-washing. In outbreaks of unknown etiology, determining and verifying the diagnosis may take an abundance of time or resources.

Outbreaks of infectious diseases that are transmittable or communicable are problematic. An infection is an invasion of an organism's body tissues by disease-causing agents, their multiplication, and the reaction of host tissues to the infectious agents and the toxins they produce. An infectious disease is an illness resulting from an infection. Infectious diseases include viruses and related agents (e.g. Rabies virus, Ebolavirus, HIV), bacteria (e.g. Salmonella), fungi, prions, parasites, and arthropods. Infectious diseases can be spread directly or indirectly from one person to another, and may include zoonotic diseases of animals that can cause disease when transmitted to humans.

For example, the Ebola disease is a severe and often fatal illness (the average Ebola case fatality rate is around 50%) in humans. The virus may be transmitted to people from wild animals and then spread from human to human. Early supportive care with rehydration improves one's chance of survival. Five species of Ebola have been identified (e.g. Bundibugyo ebolavirus, Zaire ebolavirus, and Sudan ebolavirus). Of the 25 outbreaks since 1976, these outbreaks have occurred mostly in central Africa. The incubation period for Ebola is 2-21 days. Humans are not infectious until symptoms have developed. The symptoms include fever, fatigue, muscle pain, headache, sore throat, vomiting, diarrhea, rashes, impaired kidney and liver function, and spontaneous bleeding internally and externally.

Susceptibility to infectious diseases makes it highly desirable that certain people take special care in avoiding getting infected or seek medical assistance at the earliest stages. It would also be highly desirable in these situations to have a system that identifies susceptible sections of a population and preemptively warns them.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present disclosure is defined by the claims as supported by the Specification, including the Detailed Description.

One aspect of the present disclosure relates to a method for automated susceptibility identification and alerting. An occurrence of an outbreak of an infectious disease occurring at a particular time or time range and at a particular location is determined. In response to determining the occurrence of the outbreak, patient information comprising location information and medical history information is automatically scanned. Patients who are within a predetermined range of the particular location of the outbreak and who have at least one high risk factor corresponding to the outbreak are identified using the patient information. A notification is provided to at least one of the patients who are within the predetermined range and who have the at least one high risk factor corresponding to the outbreak. The notification comprises a representation of an increased risk to the outbreak.

In another aspect, the present disclosure relates to a non-transitory computer-readable storage medium having instructions embodied thereon, the instructions being executable by one or more processors to perform a method for automated susceptibility identification and alerting. An occurrence of an outbreak of an infectious disease occurring at a particular time or time range and at a particular location is determined. In response to determining the occurrence of the outbreak, patient information comprising location information and medical history information is automatically scanned. At least one high risk factor corresponding to the outbreak is determined. Based at least in part on the patient information, patients who are at a distance above a threshold from the particular location and who have the at least one high risk factor are identified. In response to identifying the patients, an alert to at least one of the patients who are at the distance above the threshold and who have the at least one high risk factor is provided.

In yet another aspect, the present disclosure relates to a system for automated susceptibility identification and alerting. An occurrence of an outbreak of an infectious disease occurring at a particular time or time range and at a particular location is determined. In response to determining the occurrence of the outbreak, a database for location information relating to the occurrence of the outbreak and electronic medical record ("EMR") data are automatically scanned. At least one high risk factor corresponding to the outbreak based on at least one electronic literature source is determined. A patient from the EMR data who is at a distance above a threshold from the particular location of the outbreak and who has the at least one high risk factor is identified. In response to identifying the patient, a notification to the patient or a caretaker of the patient having the distance above the threshold from the particular location of the outbreak and the at least one high risk factor is provided.

BRIEF DESCRIPTION OF THE DRAWINGS

Illustrative aspects of the present invention are described in detail below with reference to the attached drawing figures, and wherein.

DETAILED DESCRIPTION

Figure 1:
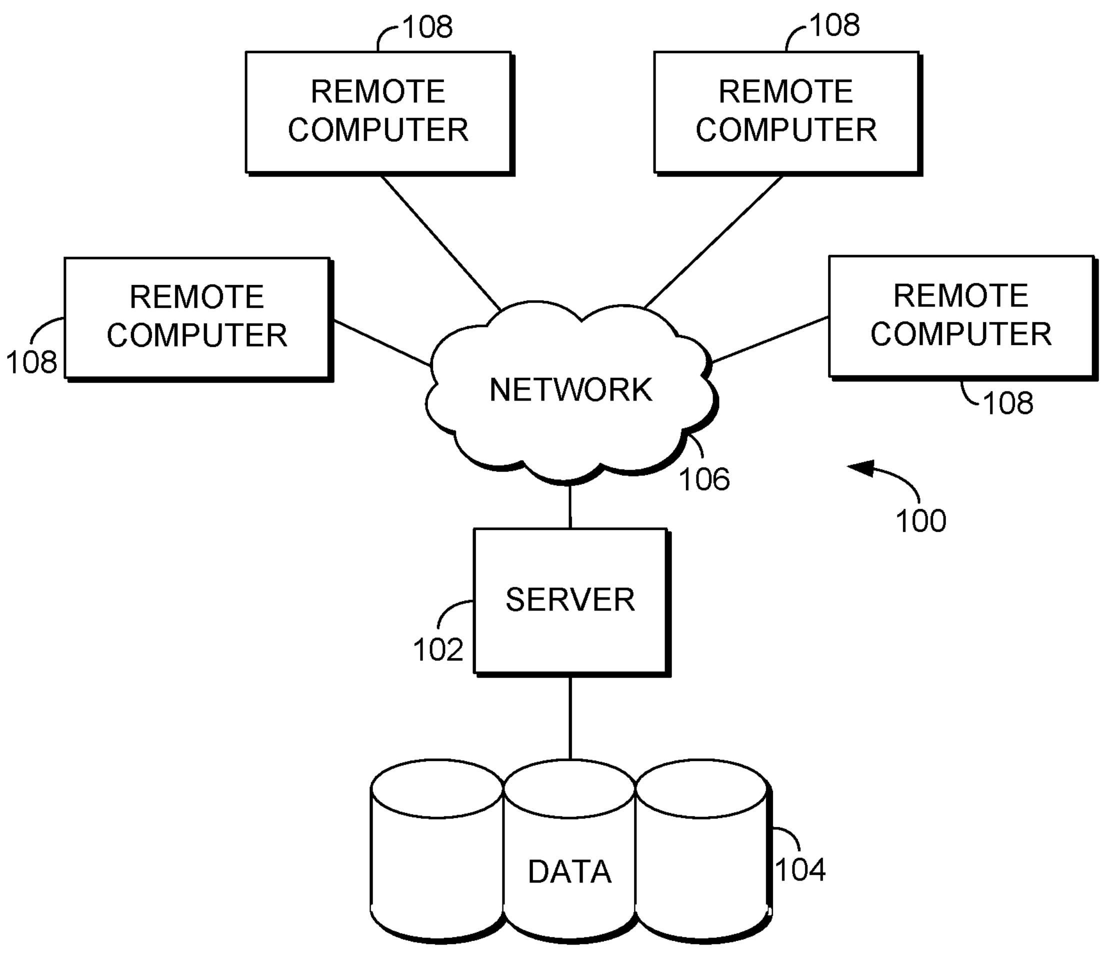
FIG. 1 illustrates a computing environment, in accordance with aspects.

The subject matter of the present invention is being described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Terms should not be interpreted as implying any particular order among or between various steps herein disclosed unless and except when the order of individual steps is explicitly described. As such, although the terms "step" and/or "block" can be used herein to connote different elements of system and/or methods, the terms should not be interpreted as implying any particular order and/or dependencies among or between various components and/or steps herein disclosed unless and except when the order of individual steps is explicitly described. The present disclosure will now be described more fully herein with reference to the accompanying drawings, which may not be drawn to scale and which are not to be construed as limiting. Indeed, the present invention can be embodied in many different forms and should not be construed as limited to the aspects set forth herein. Further, it will be apparent from this Detailed Description that the technological solutions disclosed herein are only a portion of those provided by the present invention. As such, the technological problems, solutions, advances, and improvements expressly referenced and explained herein should not be construed in a way that would limit the benefits, improvements, and/or practical application of the discussed aspects of the present invention.

Accordingly, a system, method, or medium for automated susceptibility identification and alerting provides numerous advancements over prior systems, methods, and media. As one example, the present disclosure may access publicly available real-time databases to indicate a location of the nearest infectious disease case to a patient's home address, current location, etc. As another example, the present disclosure automatically scans electronic medical record ("EMR") data and identifies people who have high risk factors or co-morbidities corresponding to the infectious disease (e.g. people within a particular age range), and issues alerts or notifications to those people or their caregivers. These alerts and notifications provide precautions to the recipient, which lead to reduced incidences of infections, complications, hospitalizations, and mortality events. Early notification targeting a susceptible population having high risk factors or co-morbidities corresponding to a nearby outbreak of an infectious disease can reduce mortality rates.

In addition to saving lives, embodiments in the present disclosure reduce burdens on the healthcare system and result in millions of dollars of savings in healthcare expenses. Automatic notification provided by embodiments in the present disclosure does not require additional manual efforts, which relieves clinicians from working to notify patients rather than spending time caring for patients. Additionally, sending alerts or notifications to patients directly increases the chances that the patients will have actual notice of the alert or warning rather than learning of an outbreak through word-of-mouth or news stations. Actual notice to patients or their caregivers enables them to take precautionary measures at early stages. Furthermore, by alerting or notifying the patients of a nearest positive case, patients can avoid the specific location of the nearest positive case. Further, providing education materials to patients based on the particular outbreak (e.g. helpline numbers) helps patients to make informed decisions and to take the proper precautionary measures needed.

Prior systems do not provide such features discussed above. For example, prior systems do not apply alerts or notifications to a susceptible population having high risk factors or co-morbidities corresponding to a nearby outbreak. Further, prior systems do not apply methods for detecting changes in trends and do not apply actions that result in intervention. Prior systems merely rely on in-depth reviews of new data by epidemiologists, which are not performed quickly or systematically. Additionally, prior systems merely focus on trend reporting over a period of time rather than alerting or notifying a susceptible population having high risk factors or co-morbidities corresponding to the nearby outbreak.

Beginning with FIG. 1, a computing environment 100 that is suitable for use in implementing aspects of the present invention is depicted. The computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein. Generally, in aspects, the computing environment 100 is a medical-information computing-system environment. However, this is just one example and the computing environment 100 can be operational with other types, other kinds, or other-purpose computing system environments or configurations. Examples of computing systems, environments, and/or configurations that might be suitable for use with the present invention include personal computers, server computers, hand-held or laptop devices, wearable devices, multiprocessor systems, microprocessor-based systems, set top boxes, programmable consumer electronics, network PCs, minicomputers, mainframe computers, distributed computing environments that include any of the above-mentioned systems or devices, and the like.

In aspects, the computing environment 100 can be described in the general context of computer instructions, such as program modules, applications, and/or extensions, being read and executed by a computing device. Examples of computer instructions can include routines, programs, objects, components, and/or data structures that perform particular tasks or implement particular abstract data types. The aspects discussed herein can be practiced in centralized and/or distributed computing environments, i.e., where computer tasks are performed utilizing remote processing devices that are linked through a communications network, whether hardwired, wireless, or a combination thereof. In a distributed configuration, computer instructions might be stored or located in association with one or more local and/or remote computer storage media (e.g., memory storage devices). Accordingly, different portions of computer instructions for implementing the computer tool in the computing environment 100 may be executed and run on different devices, whether local, remote, stationary, and/or mobile.

With continued reference to FIG. 1, the computing environment 100 comprises one or more computing devices in the form of server(s) 102, shown in the example form of a server. Although illustrated as one component in FIG. 1, the present invention can utilize a plurality of local servers and/or remote servers in the computing environment 100. Exemplary components of the server(s) 102 comprise a processing unit, internal system memory, and a suitable system bus for coupling various components, including electronic storage, memory, and the like, such as a data store, a database, and/or a database cluster. Example components of the server(s) 102 include a processing unit, internal system memory, and a suitable system bus for coupling various components, including a data store 104, with the server(s) 102. An example system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server(s) 102 typically includes therein, or has access to, a variety of non-transitory computer-readable media. Computer-readable media can be any available media that might be accessed by server(s) 102, and includes volatile, nonvolatile, removable, and non-removable media. By way of example, and not limitation, computer-readable media may comprise computer storage media and communication media. Computer storage media includes both volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can be accessed by control server 102. Computer storage media does not comprise signals per se. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above should also be included within the scope of computer-readable media.

Server(s) 102, in some embodiments, represent a stand-alone computer or computing system, such as a mainframe, blade server, and the like. Alternatively, in some embodiments, the server(s) 102 represent a set of distributed computers, such as multiple cloud computing nodes where data is provisioned or exchanged between the cloud computing nodes. The server(s) 102 might operate in a network 106 using logical connections to one or more remote computers 108. In some aspects, the one or more remote computers 108 can be located at a variety of locations, such as medical facilities, research environments, and/or clinical laboratories (e.g., molecular diagnostic laboratories), as well as hospitals, other inpatient settings (e.g., surgical centers), veterinary environments, ambulatory settings, medical billing offices, financial offices, hospital administration settings, home healthcare environments, and/or clinicians' offices). As used herein, "clinicians," "medical professionals," or "healthcare providers" can include: physicians; specialists such as surgeons, radiologists, cardiologists, and oncologists; emergency medical technicians; physicians' assistants; nurse practitioners; health coaches; nurses; nurses' aides; pharmacists; dieticians; microbiologists; laboratory experts; laboratory technologists; genetic counselors; researchers; veterinarians; students; and the like.

Computer network(s) 106 comprise a local area network (LANs) and/or a wide area network (WAN). Such networking environments are commonplace in offices, enterprise-wide computer networks, intranets, and the Internet. When utilized in a WAN networking environment, the server(s) 102 might comprise a modem or other means for establishing communications over the WAN, such as the Internet. In a networking environment, program modules or portions thereof might be stored in association with the server(s) 102, the data store 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., server(s) 102 and remote computers 108) might be utilized.

The network 106 can include an entity-wide network, campus-wide network, an office-wide network, an enterprise-wide networks, and the Internet. In the network 106, applications, extensions, program modules or portions thereof might be stored in association with the server(s) 102, the data store 104, and any of the one or more remote computers 108. For example, various application programs can reside on the memory associated with any one or more of the remote computers 108. In the computing environment 100, which is illustrated as being a distributed configuration of the network 106, the components and devices can communicate with one another and can be linked to each other using a network 106. It will be appreciated by those of ordinary skill in the art that the network connections shown are exemplary and other means of establishing a communications link between the computers (e.g., server(s) 102 and remote computers 108) might be utilized.

In operation, an organization might enter commands and information, for example, directly in peer-to-peer or near-field communication, or through the network 106 using telecommunications or Wi-Fi. Other input devices comprise microphones, satellite dishes, scanners, or the like. Commands and information might also be sent directly from a remote healthcare device. In addition to a screen, monitor, or touchscreen component, remote computers 108 might comprise other peripheral output devices, such as speakers and printers. Further, in aspects where the network 106 is distributed in configuration, the one or more remote computers 108 may be located at one or more different geographic locations (e.g. located across various locations such as buildings in a campus, medical and research facilities at a medical complex, offices or "branches" of a banking/credit entity, or can be mobile devices that are wearable or carried by personnel, or attached to vehicles or trackable items in a warehouse, for example).

Turning to the data store 104, the data store 104 may be implemented using multiple data stores that are communicatively coupled to one another, independent of the geographic or physical location of a memory device. The data store 104 may also be implemented using a single data store component or may be in the cloud. The data store 104 can, for example, store data in the form of artifacts, server lists, properties associated with servers, environments, properties associated with environments, computer instructions encoded in multiple different computer programming languages, deployment scripts, applications, properties associated with applications, release packages, version information for release packages, build levels associated with applications, identifiers for applications, identifiers for release packages, users, roles associated with users, permissions associated with roles, workflows and steps in the workflows, clients, servers associated with clients, attributes associated with properties, audit information, and/or audit trails for workflows. The data store 104 can, for example, also store data in the form of electronic records, such as electronic medical records of patients, patient-specific documents and historical records, transaction records, billing records, task and workflow records, chronological event records, and the like. Generally, the data store 104 includes physical memory that is configured to store information encoded in data. For example, the data store 104 can provide storage for computer-readable instructions, computer-executable instructions, data structures, data arrays, computer programs, applications, and other data that supports the functions and actions to be undertaken using the computing environment 100 and components shown in the example of FIG. 1.

As shown in the example of FIG. 1, when the computing environment 100 operates with distributed components that are communicatively coupled via the network 106, computer instructions, applications, extensions, and/or program modules can be located in local and/or remote computer storage media (e.g., memory storage devices). Aspects of the present invention can be described in the context of computer-executable instructions, such as program modules, being executed by a computing device. Program modules can include, but are not limited to, routines, programs, objects, components, and data structures that perform particular tasks or implement particular abstract data types. Although internal components of the devices in FIG. 1 are not illustrated, those of ordinary skill in the art will appreciate that internal components and their interconnection are present in the devices of FIG. 1. Accordingly, additional details concerning the internal construction device are not further disclosed herein. Although many other internal components of the server(s) 102 and the remote computers 108 are not shown, such components and their interconnection are known. Accordingly, additional details concerning the internal construction of the server(s) 102 and the remote computers 108 are not further disclosed herein.

Additionally, it will be understood by those of ordinary skill in the art that the computing environment 100 is just one example of a suitable computing environment and is not intended to limit the scope of use or functionality of the present invention. Similarly, the computing environment 100 should not be interpreted as imputing any dependency and/or any requirements with regard to each component and combination(s) of components illustrated in FIG. 1. It will be appreciated by those having ordinary skill in the art that the connections illustrated in FIG. 1 are also examples as other methods, hardware, software, and devices for establishing a communications link between the components, devices, systems, and entities, as shown in FIG. 1, can be utilized in implementation of the present invention. Although the connections are depicted using one or more solid lines, it will be understood by those having ordinary skill in the art that the example connections of FIG. 1 can be hardwired or wireless, and can use intermediary components that have been omitted or not included in FIG. 1 for simplicity. As such, the absence of components from FIG. 1 should be not be interpreted as limiting the present invention to exclude additional components and combination(s) of components. Moreover, though devices and components are represented in FIG. 1 as singular devices and components, it will be appreciated that some aspects can include a plurality of the devices and components such that FIG. 1 should not be considered as limiting the number of a device or component.

Figure 2:
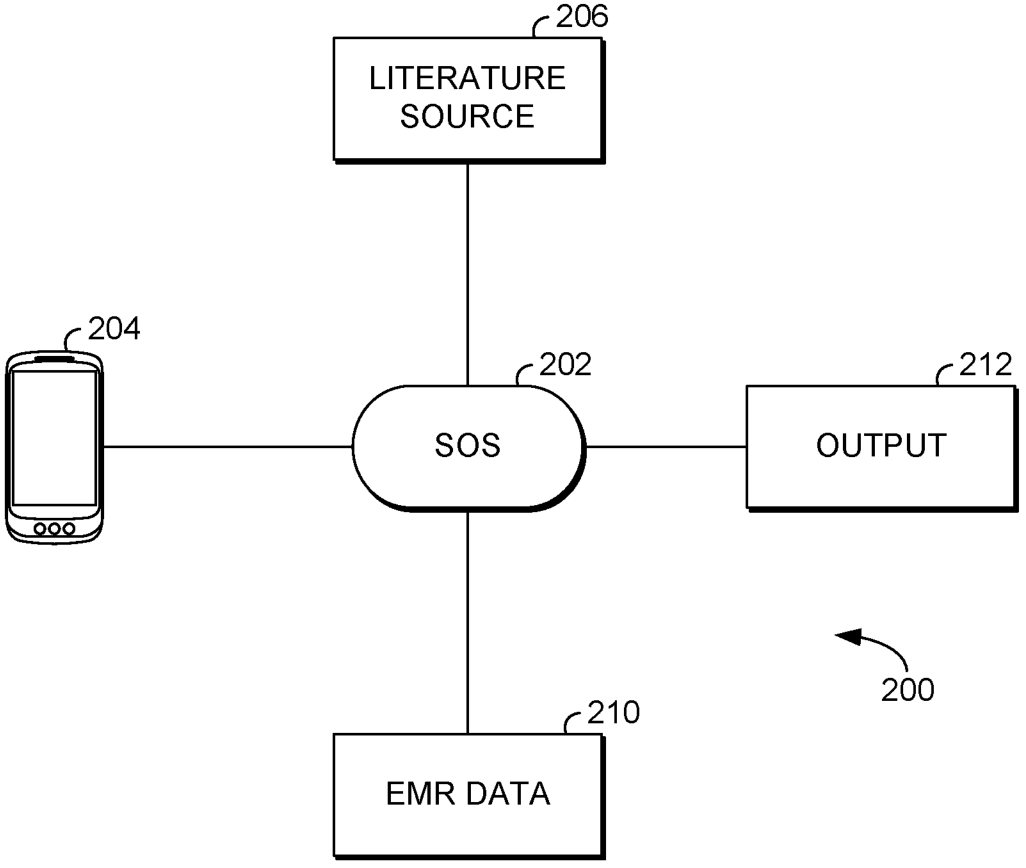
FIG. 2 depicts an exemplary susceptibility observer system, in accordance with aspects.

Turning now to FIG. 2, an example of a system is discussed. Example system 200 can be performed via one or more of the devices, components, and/or component interactions previously described in FIG. 1. It should be understood that the methods discussed herein can be implemented or performed via the execution of non-transitory computer-readable instructions and/or executable program code portions stored on computer readable media, using one or more processors. The computer-readable program code can correspond to the application, described above, wherein the application performs the methods, in some aspects. In aspects, the methods can be implemented and performed using a computerized application. As such, the methods may be computer-implemented methods integrated with and executed to complement a computerized clinical workflow.

Example system 200 comprises a Susceptibility Observer System 202, which is in communication with a computing device 204, a literature source 206, a health source 208, and EMR data 210 from an EMR. Beginning with the computing device 204, computing device 204 may comprise a cell phone, a personal computer, a server computer, other handheld or laptop devices, a wearable device (e.g. smartwatches, smart eyewear, fitness trackers, smart clothing, wearable cameras, wearable medical devices, etc.), and the like, for example. In some embodiments, the computing device 204 comprises transceivers for transmitting and receiving the navigation-related data wirelessly using a communication technology such as infrared signaling, cellular technology (whether digital and/or analog), Bluetooth technology, or microwave technology over LANs/WANs. In some embodiments, the navigation-related data includes, but is not limited to, automobile navigation data, marine craft navigation data, pedestrian navigation data, and/or hiking navigation data.

Examples of types of data the computing device 204 may collect include heart rate, calories burned, steps taken and the pace at which the steps were taken, blood pressure, releases of certain biochemical, total time spent exercising, an occurrence of a seizure, etc. Further, other types of data the computing device 204 may collect include application information that is accessible by the Susceptibility Observer System 202, the application information comprising diet tracking information comprising daily calorie intake, daily dairy intake, nutritional intake per day, and the like. Other application information may include tracked fitness information, such as steps taken within certain intervals and the pace at which the steps were taken. Other application information may include sleep information comprising a sleep pattern, a quality of sleep during each night, and an amount of sleep during each night.

The computing device 204 may transmit information collected and received to the Susceptibility Observer System 202. This information may comprise a state in response to receiving a transmission. Examples of the state in response to receiving the transmission may include places a user has visited; connections, followers, and followees of accounts the user has; songs heard; products viewed; etc. Further, logging information such as time stamps associated with various occurrences may also be transmitted to the Susceptibility Observer System 202. Computing device 204 may have healthcare application information that is accessible by the Susceptibility Observer System 202. Healthcare application information may include insurance coverage information, scheduled appointments and location of the appointments, medication information about medications being taken (e.g. when a refill is due, where medications are picked up at, whether a medication has not been taken during a period of time), patient task information such as whether an assigned task has been completed and when it was completed, personal health history portals, referral networks, doctor rankings and education, and peer-reviewed disease content, for example.

Additionally, the computing device 204 may transmit location information to Susceptibility Observer System 202. Location information may comprise positioning information (e.g., coordinates) of a vehicle of a user or of a previous or current location of a device of the user, a parking structure floor number, GPS data, latitude and longitude coordinates, boundary information corresponding to real property, and/or the like. Location information may also comprise an absolute position and/or a relative position of the computing device 204. For example, relative positioning of a computing device 204 may be obtained via beacon transmission and response, triangulation from WiFi connections, GNSS signals, ultrasound sensors, and/or inertial sensors of the computing device 204. The location information, for example, may also comprise altitude information ascertained from GNSS signals and a GNSS receiver of the computing device 204. In some embodiments, the location information may include relative location information ascertained from a previously determined location by multi-axis accelerometers. For example, a change in position from a first location at a first time to a second location at a second time may be determined by manipulating accelerometer sensor output (e.g. by performing an algorithm including determining a double integral with respect to time of the accelerometer sensor output for each of the multiple axes). Additionally, in some embodiments, the location information may be subject to sharing restrictions. Accordingly, a policy database may be queried to retrieve sharing information and it may be determined that user preferences permit sharing of the location information.

Additionally, the location information may comprise addresses entered into an electronic address book comprising a compilation of records including one or more person profiles or a list of properties owned by a user of the address book. Additionally, location information may comprise information from a navigation application, such as most frequent destinations visited, most recent destinations, and other saved locations (e.g. "home" and "work"). Location information may also comprise contact information associated with existing contacts, which may be collected or updated from outside sources (e.g., a search engine that accessible by or part of routines associated with the address book). Further, the outside sources may include information gathered from company web sites, personal web sites, social network web pages or other information sources (e.g., photo or video sharing websites, person search directory pages, travel websites, online retailers, and maps and directions websites).

Turning to the literature source 206, literature source 206 may comprise current information on susceptibility and risk factors corresponding to the outbreak. For example, literature source 206 may comprise sources such as Pubmed (https://www.ncbi.nlm.nih.gov/pubmed/), World Health Organization (https://www.who.int/), Centers for Disease Control and Prevention (https://www.cdc.gov/), John Hopkins University (https://wwwjhu.edu/), Mayo Clinic (http://mayoclinic.org/), and other literature sources 206 using various technologies. In some embodiments, literature sources 206 may also comprise a particular news source (e.g. New York Times) or a particular state or county dashboard that tracks an outbreak (e.g. Jackson County, NC COVID-19 Dashboard or COVID-19 in Texas Dashboard).

In some embodiments, a selection of the literature source 206 is made for determining the occurrence of an outbreak. For example, a literature source 206 from the Centers for Disease Control and Prevention (CDC) can provide data that may provide insight as to whether a certain strain of disease is more prevalent than normal. For example, the selection of the literature source may be to a local literature source 206 (e.g. Jackson County, NC COVID-19 Dashboard). In some embodiments, the selection is for sources only related to a particular country. In some embodiments, the selection may exclude particular sources based on regions being monitored or based on the entity monitoring. In some embodiments, the selection may be restricted to university sources only. In some embodiments, the selection may include a national health source, a global health source, a local health source, and a university source.

Further, upon determining an occurrence of an outbreak of a particular infectious disease occurring at a particular time or time range and at a particular location based on a selection that an outbreak has occurred or based on the literature source 206, the Susceptibility Observer System 202 may automatically scan the literature sources 206. Automatically scanning the literature sources 206, unlike prior systems and methods, does not depend on a manual entry that is fed to the Susceptibility Observer System 202. For instance, literature source 206 may be scanned for location information relating to the occurrence of the outbreak and for information relating to susceptibility and risk factors corresponding to the outbreak. In some embodiments, a selection of the literature source 206 is made for determining susceptibility and risk factors corresponding to the outbreak, wherein determining the susceptibility and risk factors is based in part or solely on the selected literature source(s) 206.

In some embodiments, Susceptibility Observer System 202 may use cognitive computing to scan the literature sources 206 for susceptibility and risk factors corresponding to the outbreak. Using the cognitive computing may comprise defining complex analytics in which patterns and trends related to the susceptibility and risk factors are established and generated and can interact with other elements of the Susceptibility Observer System 202. In some embodiments, using the cognitive computing may comprise communicating with an application programming interface (API) or an application that receives requests from the Susceptibility Observer System 202 to modify rules for analyzing susceptibility and risk factors. In some embodiments, the cognitive computing may be enriched by context data relating to the outbreak for an in-depth cognitive predictive analytics analysis.

Examples of context data relating to the outbreak may include date, hour, and location of the information from the literature sources 206. As another example, the context data may include demographic information and syntax data, which may also assist with weighing any conflicting evidence among the literature sources 206. As another example, the context data may include image data, structured and unstructured data, or user profile data. In addition, context data may be used for the determination of a goal of a literature source 206 or a particular webpage of a literature source 206, which may be used to assist with weighing any conflicting evidence among various literature sources for determining susceptibility and risk factors corresponding to the outbreak.

In some embodiments, the cognitive computing comprises artificial intelligence logic, such as natural language processing (NLP) based logic, for example, and machine learning logic, which may be provided as software executed on hardware, specialized hardware, or any combination of the specialized hardware and the executed software. This logic may implement a model(s) (e.g. a neural network model, a machine learning model, a deep learning model, etc.) that may be trained for particular purposes for supporting the particular cognitive operations. Additionally, the logic may implement operations including answering questions, identifying related concepts within different portions of content in a corpus, intelligently searching algorithms (e.g. Internet web page searches), generating recommendations (e.g. a particular vitamin intake for a particular user), and the like.

In some embodiments, the Susceptibility Observer System 202 receives an input question (e.g. how does the age, diet information, and family history of this particular patient change this particular patient's risk or susceptibility to the outbreak), parses the input question to extract major features of the question, uses the extracted major features to formulate queries, and then applies those queries to the corpus of data. The Susceptibility Observer System 202 may then generate a set of hypotheses or potential answers to the input question by scanning across the corpus of data for portions of the corpus of data that have a potential to contain a valuable answer to the input question. The Susceptibility Observer System 202 may then perform deep analysis on language of the input question and language in each of the portions of the corpus of data found during the queries using reasoning algorithms (e.g. comparisons, natural language analysis, lexical analysis, etc.) to generate a score. In embodiments, a reasoning algorithm may match terms and synonyms within the language of the input question and the portions of the corpus of data found during the queries. In embodiments, a reasoning algorithm may look at temporal or spatial features in the language. In embodiments, a reasoning algorithm may evaluate the source of the portion of the corpus of data and evaluate its veracity (e.g. by comparing it to a more recently updated literature source 206).

In embodiments, the score(s) generated from the reasoning algorithms may indicate an extent to which the potential answer is inferred by the input question based on a respective specific area the respective reasoning algorithm is focused. Each score generated may then be weighted against a statistical model for indicating how well the respective reasoning algorithm performed at inferring the potential answer. Continuing the example, the statistical model may additionally be used to summarize a level of confidence that the Susceptibility Observer System 202 has regarding the inference of the potential answer. This process may be repeated for each hypotheses or potential answer until the Susceptibility Observer System 202 identifies answers that surface as being significantly stronger than others. A final answer or ranked set of answers may then be generated for the input question.

Further, the Susceptibility Observer System 202 may provide updates upon occurrence of an update to the literature source 206, after a predetermined amount of time, or upon detection of an update to the literature source 206. For example, a literature source may be updated at the end of each business day or after obtaining new results. In some embodiments, the Susceptibility Observer System 202 may update the score(s) generated from the reasoning algorithms upon occurrence of an update to the literature source 206 or upon detection of an update to the literature source 206. In some embodiments, the Susceptibility Observer System 202 may update the level of confidence that the Susceptibility Observer System 202 has regarding the inference of the potential answer after an update to the literature source 206. In some embodiments, the Susceptibility Observer System 202 may update susceptibility and risk factors corresponding to the outbreak after an update to the literature source 206. In some embodiments, the Susceptibility Observer System 202 may continuously update susceptibility and risk factors based on predetermined intervals of time.

In addition, the Susceptibility Observer System 202 is in communication with an EMR comprising EMR data 210, the EMR including one or more data stores (e.g. data store 104) of health records and one or more computers or servers that facilitate the storing and retrieval of the health records. In some embodiments, the EMR comprising EMR data 210 may be implemented as a cloud-based platform or may be distributed across multiple physical locations. The EMR comprising EMR data 210 may further include record systems, which store real-time or near real-time patient (or user) information, such as wearable, bedside, or in-home patient monitors, for example, and may store patient EMR data 210. For example, the EMR comprising EMR data 210 may comprise one or a plurality of EMR systems such as hospital EMR systems, health information exchange EMR systems, ambulatory clinic EMR systems, or other systems having health-related records for one or more patients.

The plurality of EMR systems may involve EMR systems from various entities, hospitals, and departments. For example, EMR data may be retrieved for a patient from EMR systems from a primary care provider and an emergency room is different states, the EMR data retrieved comprising various formats. The various formats may include image formats, such as radiograph, computed tomography (CT), magnetic resonance imaging (MRI), Ultrasound (US), mammogram, positron emission tomography scan (PET), and nuclear scan (NM) images; montages of medical images; medical reports; voice clips, notes; and medical reports, for example. Further, EMR data may be received in other various formats, such as PDF, JPEG, GIF, PNG, DOC, XLS, PPT, MP3, WAV, HTML, XML, and various other formats. The Susceptibility Observer System 202 may receive the EMR data in various formats and may standardize the data into a standard format for analysis and transmission.

Generally, EMRs (sometimes referred to as electronic health records (EHRs)), may comprise EMR data 210 comprising electronic clinical documents such as images, clinical notes, orders, summaries, reports, analyses, information received from clinical applications and medical devices, or other types of electronic medical documentation relevant to a particular patient's condition and/or treatment. Electronic clinical documents may contain various types of information relevant to the condition and/or treatment of a particular patient and can include information relating to, for example, patient identification information, images, alert history, culture results, patient-entered information, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, clinician assignments, and a host of other relevant clinical information. Further, in some embodiments, EMR data 210 comprising patient data may include patient demographic data, such as age, sex, race, nationality, socioeconomic status, marital status, and employment status and history. This data may further include the patient's insurance information, such as the insurance provider and the type of plan. Additional patient data may include previous and current home and work addresses.

Other types of EMR data 210 comprising patient data include current patient data and historical patient data. In exemplary aspects, current patient data includes data relating to the patient's labs, vitals, diagnoses, medications from a current encounter (e.g., a current admission to a healthcare facility, a current visit to an outpatient facility, or a current period of receiving home healthcare services). The current patient data may include a diagnosis and/or treatment (including medications administered or ordered and procedures performed or ordered). During the current encounter, the patient may be diagnosed or treated with a condition such as asthma, cancer, or heart disease, for example. Current patient data may further include lab results (e.g., physiological data), including vital sign data, from the current encounter. Historical patient data may include information about the patient's past encounters at the current healthcare facility or other healthcare facilities, past encounters at a post-acute care facility, etc. In some embodiments, historical patient data includes previous diagnoses, medications, and lab results. The content and volume of such information in an EMR system are not intended to limit the scope of the present disclosure in any way.

Further, this patient data in the EMR may be received from different sources. In some embodiments, data relating to the patient's current condition and/or patient demographics may be received directly from a user, such as the patient or a care provider, inputting such information into a user device. Some current patient data, such as patient variable values, may be received from one or more sensors or monitoring devices or directly from a laboratory running the laboratory procedures. Additionally, historical patient information may be received from the patient's EMR and/or from insurance claims data for the patient. For example, EMR data from in-home care services, hospitals, or any healthcare facility may be received. In an alternative embodiment, the patient's history may be received directly from the patient, such as during registration when admitted to a care facility for the current encounter or starting the current care services (such as with in-home care services).

Turning now to output 212, the output 212 may comprise a notification, an alert, an escalated alert, a message, etc. Output 212 may be sent to patients, clinicians, caregivers, guardians, and the like, in various modes of communication including email notifications, short text messages to cell phones, tablets, smart watches, or pagers. In some embodiments, an instant message may be sent providing a personal output 212 with detailed information on ways to avoid contracting the outbreak specific to the patient being notified, such as taking a particular set of vitamins and probiotics and wearing a mask. In some embodiments, output 212 is sent when the patient is entering a location where a previous individual contracted the infectious disease within a predefined amount of time prior to the patient entering the location. In some embodiments, output 212 may include a recommended drug or test.

Figure 3:
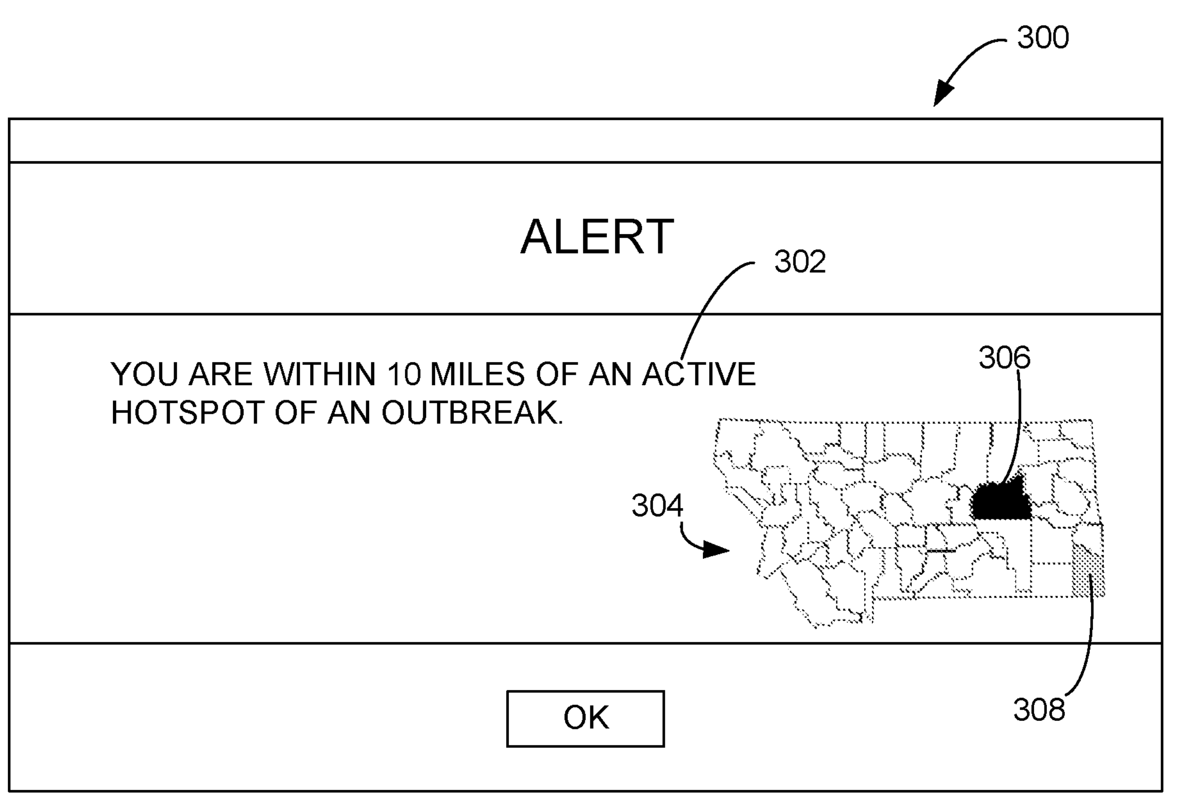
FIG. 3 depicts an exemplary alerting environment, in accordance with aspects.

Turning now to FIG. 3, a graphical user interface may display an example alert 300 that may comprise an example message 302 and a map 304. In some embodiments, the alert may be an audio alert, haptic feedback (e.g. a vibration), or both. The alert may also comprise a blinking light. In some embodiments, the example message 302 may indicate that an outbreak has occurred, the type of infectious disease, information about how transmittable the disease is, modes of transmission, and the like. Further, the example message 302 may indicate a recipient is within a certain distance from the outbreak. In some embodiments, the example message 302 may indicate a location of a closest occurrence of the outbreak to a location (e.g. home address or current location) of the recipient. The closest occurrence may be an area, a store, an address, a county, etc. In some embodiments, the example message 302 may indicate a high risk factor to susceptibility to contracting the disease, a potential risk factor to susceptibility to contracting the disease, and mitigating factors to susceptibility to contracting the disease. For example, a high risk factor for COVID-19 may be chronic kidney disease, a potential risk factor for COVID-19 may be dementia, and a mitigating factor for COVID-19 may be maintaining a two meter distance from others and properly wearing a face mask.

In some embodiments, the alert 300 may comprise extremely-high-risk area notifications 306 and high-risk area notifications 308. Risk levels may be determined based on a number of active cases, a rate at which a population is contracting the infectious disease, or a number of active cases within a certain area and based on the population within that certain area, for example. Additionally, the example alert 300 may also provide an example message 302 with information for educating the recipient on the particular outbreak, helpline numbers, what symptoms to be on the lookout for, and actions to take in the event of developing symptoms. For example, if the outbreak of the infectious disease is Ebola, the message 302 may provide a link to the "treatment and prevention" page from the World Health Organization or the message 302 may provide the top symptoms of Ebola to be on the lookout for.

In some embodiments, the alert 300 may be delivered to a guardian or caretaker of an individual. In embodiments where the alert 300 or notification comprises a message 302 having personal medical information of the individual, the alert 300 or notification may be received by those having permission to receive the patient's EMR data 210 or those having permission to receive the message 302 having personal medical information of the individual. In one embodiment, those that have permission may be family members, friends, acquaintances, guardians and the like.

Further, in some embodiments, an escalated alert may be provided. For example, the escalated alert may be provided to a patient who is at a distance above a threshold from the location of the outbreak. In addition, the escalated alert may be provided to a patient who is highly susceptible to the infectious disease (e.g. someone with multiple high risk factors of susceptibility and heighted symptoms). In some embodiments, the escalated alert comprises information for actions to take during emergencies. In some embodiments, the escalated alert comprises a message notifying the recipient that a clinician or an emergency service has been notified. In some embodiments, the escalated alert comprises notification to an emergency medical service (e.g. an ambulance service).

Figure 4:
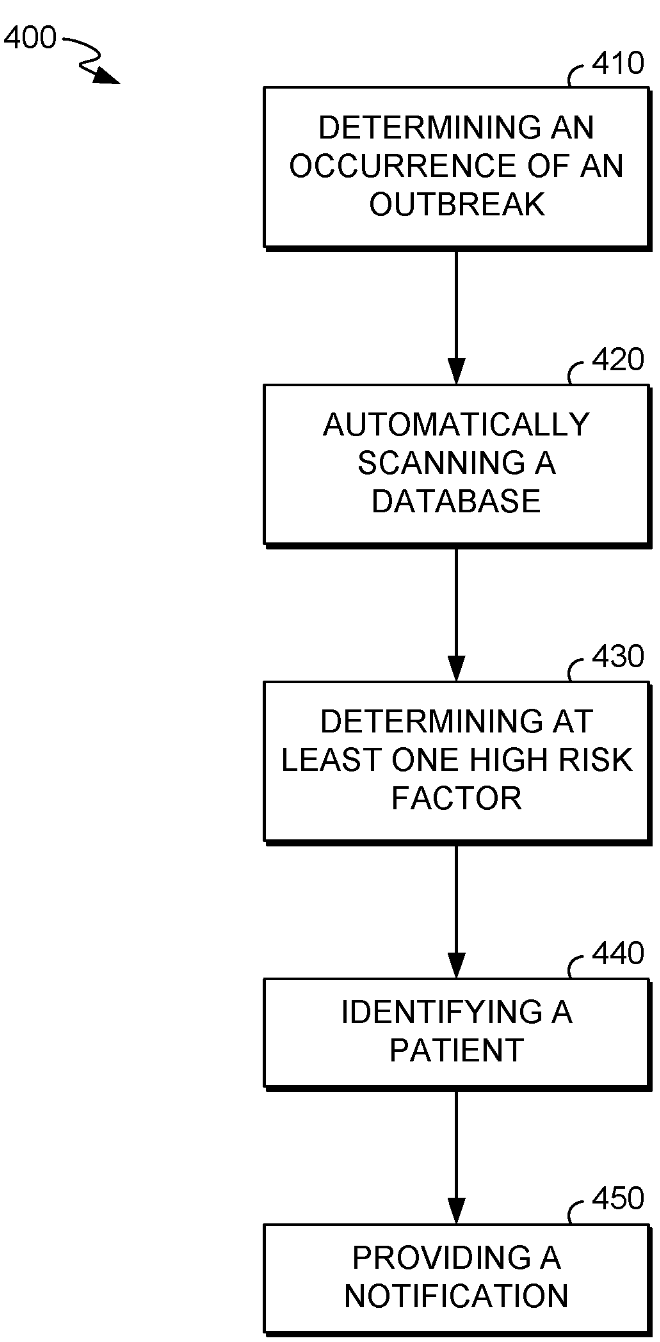
FIG. 4 depicts a flowchart in accordance with aspects of the disclosure.

Turning now to FIG. 4, flow diagram 400 comprises determining an occurrence of an outbreak 410, automatically scanning a database 420, determining at least one high risk factor 430, identifying a patient 440, and providing a notification 450. Beginning with determining the occurrence of the outbreak 410, the occurrence of the outbreak 410 may be determined from at least one electronic literature source (e.g. literature source 206 discussed in FIG. 2) or by a received selection that an occurrence of an outbreak occurred. For example, a selection may be received after a spike in admissions to a hospital, the admissions comprising patients with at least one similar symptom. As another example, the occurrence of the outbreak may be determined after identifying a cluster of recently admitted patients with a particular disease pattern. In yet another example, the occurrence of the outbreak may be determined after detection of an atypical age distribution for an otherwise common disease (e.g. an outbreak of what initially appeared to be chickenpox among adults). Further, the outbreak may be of an infectious disease, such as influenza, common cold, severe acute respiratory syndrome, *E. coli*, pneumonia, tuberculosis, malaria, viral hepatitis, Lyme disease, etc.

In some embodiments, the occurrence of the outbreak 410 of the infectious disease occurs at a particular time or time range and at a particular location. The particular time or time range and the particular location may be determined using a public database of at least one hotspot of the outbreak. In some embodiments, the particular time range may be for an incubation period for the infectious disease. In some embodiments, the particular location may comprise a town, a county, a city, a particular neighborhood, a nation, a state, and the like. In some embodiments, the particular location may comprise a certain area within a county, city, etc. In some embodiments, the particular location may span across multiple counties or may span between a portion of at least two counties, for example. In some embodiments, determining the particular location may be based on a particular area exceeding a particular threshold number or population percentage of cases, for example.

Turning now to automatically scanning the database 420, the database may comprise EMR data including patient records having structured and unstructured data sources (e.g. EMR data 210 in FIG. 2 discussed above). The structured data sources may include a plurality of databases, such as a laboratory database, a prescription database, and a test result database, for example. The unstructured data sources may include, for example, information in text format (such as treatment notes, admission slips, and reports), image information, and waveform information. In embodiments, patient tracking information may comprise information from an emergency room, a hospital room, a hospice room, an intensive care unit, radiology, etc.

In embodiments, patient information comprising location information and medical history information is automatically scanned. In some embodiments, an EMR is scanned for the location information and the medical history information. In some embodiments, an EMR and a computing device (e.g. smartphone or smartwatch) are scanned for the location information and the medical history information. Further, the database may be automatically scanned for location information relating to the occurrence of the outbreak, and EMR data may also be scanned for the location information or other information. For example, patients who have contracted the infectious disease may have home addresses saved in the EMR, which may be automatically scanned for location information relating to the occurrence of the outbreak. In some embodiments, the automatic scanning comprises utilizing cognitive computing, as discussed in FIG. 2. In some embodiments, the database scanned comprises a publicly accessible database (e.g. electronic literature source 206), which is scanned for information relating to the outbreak, such as hotspots information to identify a geo-location of disease cases.

Turning now to determining the high risk factor 430, determining or identifying the at least one high risk factor may be based on the electronic literature source, which may be periodically updated. For example, if the outbreak was severe acute respiratory syndrome, the at least one high risk factor may comprise at least one of cardiovascular and kidney diseases, obesity, cognitive and neurological disorders in individuals over 65 years of age, pregnancy status, ethnicity, age, co-morbidities, geographical location, environmental factors, social behavior, food habits, physical activity, and hypertension. In some embodiments, the high risk factor will have contributed to a percentage of mortality of a population. Continuing the example, in some embodiments, the percentage of morality that the high risk factor contributed to was above a threshold. In some embodiments, the high risk factor comprises a particular age group.

In some embodiments, a plurality of high risk factors may be identified or determined and a plurality of probable risk factors may be identified or determined. To illustrate, according to the CDC during Oct. 6, 2020, current data supported the increasing risk of severe illness from the COVID-19 virus among adults who have certain underlying medical conditions. For example, adults of any age with the following conditions are at increased risk of severe illnesses from the virus that causes COVID-19: cancer, chronic kidney disease, chronic obstructive pulmonary disease, heart conditions (e.g. heart failure, coronary artery disease, cardiomyopathies), immunocompromised state from solid organ transplant, obesity (having a body mass index of 30 $kg/m^2$ or higher but less than 40 $kg/m^2$), severe obesity (having a body mass index over 40 $kg/m^2$), sickle cell disease, smoking, type 2 diabetes mellitus.

Further, adults of any age with the following conditions might be at an increased risk of severe illnesses from the virus that causes COVID-19: asthma; cerebrovascular disease; cystic fibrosis; immunocompromised state from blood or bone marrow transplant, immune deficiencies, HIV, use of corticosteroids, or use of other immune weakening medicines; neurologic conditions (e.g. dementia); liver disease; overweight (having a body mass index of 25 $kg/m^2$ or higher but less than 30 $kg/m^2$; pregnancy; pulmonary fibrosis; thalassemia; and type 1 diabetes mellitus. Additionally, children with the following conditions might be at increased risk for severe illness: obesity, medical complexity, severe genetic disorders, severe neurologic disorders, inherited metabolic disorders, congenital heart disease, diabetes, asthma and other chronic lung disease, and immunosuppression due to malignancy or immune-weakening medications. Accordingly, a plurality of high risk factors (e.g. cancer and chronic kidney disease for COVID-19) may be identified or determined and a plurality of probable risk factors (e.g. pulmonary fibrosis and thalassemia disease for COVID-19) may be identified or determined.

Turning now to identifying the patient 440, in some embodiments, a patient who is within a predetermined range of the particular location of the outbreak and who has the at least one high risk factor corresponding to the outbreak may be identified using patient information comprising location information and medical history information. In some embodiments, the predetermined range is determined based on a distance between a detected GPS location of the at least one of the patients and the particular location of the outbreak. In some embodiments, the predetermined range is determined based on a distance between an address from electronic medical record information of the at least one of the patients and a location of a closest occurrence of the outbreak. The location of the closest occurrence may be determined using addresses from an EMR or from user device data. In some embodiments, a patient who is at a distance above a threshold from the particular location and who has the at least one high risk factor is identified. In some embodiments, the patient being identified is a patient who is currently being treated in a hospital or was previously treated in the hospital.

Turning now to providing the notification 450, a notification may be provided to at least one of the patients who are within the predetermined range and who have the at least one high risk factor corresponding to the outbreak. In embodiments, the notification may comprise a representation of an increased risk to the outbreak. The representation of the increased risk to the outbreak may comprise a percentage of the increased risk compared to patients who are within the predetermined range but who do not have the at least one high risk factor. The notification may also comprise a location of a closest occurrence of the outbreak to a location of the at least one of the patients. In some embodiments, an alert is provided to at least one of the patients who are at the distance above the threshold and who have the at least one high risk factor. An escalated alert may be provided to the patient who is at the distance above the threshold and who has the plurality of high risk factors. The escalated alert may comprise information for actions to take during emergencies or a helpline numbers. The alert may be provided to a caregiver of the at least one patient or may be provided via a healthcare application.

The present invention has now been described in relation to particular aspects, which are intended in all respects to be illustrative rather than restrictive. Thus the present invention is not limited to these aspects, but variations and modifications can be made without departing from the scope of the present invention.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

The invention claimed is:

1. A method for automated susceptibility identification and alerting, the method comprising:

determining, by a computing device, an occurrence of an outbreak of an infectious disease that is (a) transmittable from one human to another human, and (b) occurring at a particular time or time range and at a particular location;

in response to determining the occurrence of the outbreak, automatically scanning, by the computing device, a plurality of patient records stored in a database for a plurality of patients, the plurality of patient records comprising medical history information for the plurality of patients;

in response to determining the occurrence of the outbreak, automatically scanning, by the computing device, literature sources for susceptibility and risk factors corresponding to the outbreak;

generating training data, for training a neural network model, from the susceptibility and risk factors;

training the neural network model, using the training data, to determine when a patient has at least one high risk factor corresponding to the outbreak;

determining, by the computing device, a GPS location of a mobile computing device associated with a patient of the plurality of patients, wherein the GPS location of the mobile computing device is a current location of the mobile computing device as determined by a Global Positioning System;

responsive to determining that the GPS location of the mobile computing device is within a predetermined range of the particular location of the outbreak:

determining, by the computing device, that the patient, associated with the mobile computing device, is within a predetermined range of the particular location of the outbreak;

determining, by applying the trained neural network model to the plurality of patient records, that the patient has at least one high risk factor corresponding to the outbreak;

in response to determining, by the computing device, that (a) the patient is within the predetermined range of the particular location of the outbreak and (b) the patient has at least one high risk factor corresponding to the outbreak, identifying the patient as highly susceptible to the infectious disease; and in response to identifying the patient as highly susceptible to the infectious disease, automatically transmitting, by the computing device, an escalated alert to at least one computing device associated with the patient;

wherein the escalated alert comprises a percentage of an increased risk to the outbreak for (a) the patient, with the at least one high risk factor, that is within the predetermined range of the particular location of the outbreak compared to (b) patients who are within the predetermined range of the particular location of the outbreak but do not have the at least one high risk factor.

2. The method of claim 1, wherein the escalated alert comprises a location of a closest occurrence of the outbreak to a location of the patients.

3. The method of claim 1, wherein the method further comprises:

prior to determining the occurrence of the outbreak, receiving, by the computing device, a selection of the outbreak comprising one of influenza, common cold, severe acute respiratory syndrome, *E. coli*, pneumonia, tuberculosis, malaria, viral hepatitis, and Lyme disease wherein the literature sources comprise electronic literature sources, wherein at least one of the electronic literature sources is periodically updated.

4. The method of claim 3, wherein the selection of the outbreak was severe acute respiratory syndrome and the at least one high risk factor comprises at least one of cardiovascular and kidney diseases, obesity, cognitive and neurological disorders in patients over 65 years of age, pregnancy status, ethnicity, age, co-morbidities, geographical location, environmental factors, social behavior, food habits, physical activity, and hypertension, and the electronic literature sources comprising one from a local health source and one from a national health source.

5. The method of claim 1, wherein the literature sources comprise an electronic literature source that is periodically updated, wherein the at least one high risk factor contributed to a percentage of mortality of a population above a threshold.

6. The method of claim 1, wherein determining, by the computing device, the occurrence of the outbreak is based on a local health source, a national health source, or a global health source.

7. The method of claim 1, wherein the predetermined range was determined, by the computing device, based on a distance between an address from electronic medical record information of the patient and a location of a closest occurrence of the outbreak.

8. The method of claim 1, further comprising determining, by the computing device, the particular location of the outbreak using a public database of at least one hotspot of the outbreak.

9. The method of claim 1, wherein automatically scanning comprises utilizing cognitive computing.

10. One or more non-transitory computer-readable storage media having instructions embodied thereon, the instructions being executable by one or more processors to perform a method for automated susceptibility identification and alerting, the method comprising:

determining, by a computing device, an occurrence of an outbreak of an infectious disease that is (a) transmittable from one human to another human, and (b) occurring at a particular time or time range and at a particular location;

in response to determining the occurrence of the outbreak, automatically scanning a plurality of patient records stored in a database for a plurality of patients, the plurality of patient records comprising medical history information for the plurality of patients;

in response to determining the occurrence of the outbreak, automatically scanning literature sources for susceptibility and risk factors corresponding to the outbreak;

generating training data, for training a neural network model, from the susceptibility and risk factors;

training the neural network model, using the training data, to determine when a patient has at least one high risk factor corresponding to the outbreak;

determining a GPS location of a mobile computing device associated with a patient of the plurality of patients, wherein the GPS location of the mobile computing device is a current location of the mobile computing device as determined by a Global Positioning System;

responsive to determining that the GPS location of the mobile computing device is within a predetermined range of the particular location of the outbreak:

determining that the patient, associated with the mobile computing device, is within a predetermined range of the particular location of the outbreak;

determining, by applying the trained neural network model to the plurality of patient records, that the patient has at least one high risk factor corresponding to the outbreak;

in response to determining, by the computing device, that (a) the patient is within the predetermined range of the particular location of the outbreak and (b) the patient has at least one high risk factor corresponding to the outbreak, identifying the patient as highly susceptible to the infectious disease; and in response to identifying the patient as highly susceptible to the infectious disease, automatically transmitting, by the computing device, an escalated alert to at least one computing device associated with the patient;

wherein the escalated alert comprises a percentage of an increased risk to the outbreak for (a) the patient, with the at least one high risk factor, that is within the predetermined range of the particular location of the outbreak compared to (b) patients who are within the predetermined range of the particular location of the outbreak but do not have the at least one high risk factor.

11. The one or more non-transitory computer-readable storage media of claim 10, wherein determining the patient comprises patients currently being treated in a hospital and patients previously treated in the hospital, and wherein the at least one high risk factor comprises a particular age group.

12. The one or more non-transitory computer-readable storage media of claim 10, wherein automatically scanning comprises utilizing cognitive computing, and wherein the infectious disease is a virus or bacteria.

13. The one or more non-transitory computer-readable storage media of claim 10, wherein the method further comprises:

determining that a patient is at a distance above a threshold from the particular location and has a plurality of high risk factors; and providing an escalated alert to the patient who is at the distance above the threshold and who has the plurality of high risk factors, the escalated alert comprising information for actions to take during emergencies.

14. The one or more non-transitory computer-readable storage media of claim 13, wherein the distance was determined using GPS data of a user device.

15. The one or more non-transitory computer-readable storage media of claim 10, wherein the escalated alert is provided to a caregiver of the patient.

16. The one or more non-transitory computer-readable storage media of claim 10, wherein the escalated alert is provided via a healthcare application and provides a helpline number.

17. The one or more non-transitory computer-readable storage media of claim 10, wherein the literature sources comprise an electronic literature source that is periodically updated.

18. The one or more non-transitory computer-readable storage media of claim 17, wherein the method further comprises, prior to determining that the patient has the at least one high risk factor, receiving a selection of the electronic literature source that is from a global health source.

19. The one or more non-transitory computer-readable storage media of claim 17, wherein determining that the patient has at least one high risk factor corresponding to the outbreak is updated upon each detected change to the electronic literature source.

20. A system for automated susceptibility identification and alerting, the system comprising:

one or more processors; and one or more computer storage media storing computer-useable instructions that, when used by the one or more processors, cause the one or more processors to perform a method, the method comprising:

determining, by a computing device, an occurrence of an outbreak of an infectious disease that is (a) transmittable from one human to another human, and (b) occurring at a particular time or time range and at a particular location;

in response to determining the occurrence of the outbreak, automatically scanning a database for electronic medical record (EMR) data for a plurality of patients;

determining a GPS location of a mobile computing device associated with at least one patient of the plurality of patients, wherein the GPS location of the mobile computing device is a current location of the mobile computing device as determined by a Global Positioning System;

in response to determining the occurrence of the outbreak, automatically scanning, by the computing device, literature sources for susceptibility and risk factors corresponding to the outbreak;

generating training data, for training a neural network model, from the susceptibility and risk factors;

training the neural network model, using the training data, to determine when a patient has at least one high risk factor corresponding to the outbreak;

based on the GPS location of the mobile computing device and the EMR data, determining that the at least one patient is at a distance above a threshold from the particular location of the outbreak;

determining, by applying the trained neural network model to the EMR data, that the at least one patient has the at least one high risk factor;

in response to determining that (a) the at least one patient is at a distance above the threshold from the particular location of the outbreak and (b) the at least one patient has the at least one high risk factor, identifying the at least one patient as highly susceptible to the infectious disease; and in response to identifying the at least one patient as highly susceptible to the infectious disease, automatically transmitting, by the computing device, an escalated alert to at least one computing device associated with the at least one patient or a caretaker of the patient;

wherein the escalated alert comprises a percentage of an increased risk to the outbreak for (a) the at least one patient, with the at least one high risk factor, that is within a predetermined range of the particular location of the outbreak compared to (b) patients who are within the predetermined range of the particular location of the outbreak but do not have the at least one high risk factor.

* * * * *